United States Patent
Nishino et al.

(10) Patent No.: US 8,053,727 B2
(45) Date of Patent: Nov. 8, 2011

(54) RADIATION CONVERSION DEVICE AND RADIATION IMAGE CAPTURING SYSTEM USING THE SAME

(75) Inventors: Naoyuki Nishino, Minami-ashigara (JP); Yasunori Ohta, Yokohama (JP); Eiichi Kito, Minami-ashigara (JP); Hiroshi Tamaoki, Odawara (JP); Tatsuo Iiyama, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 238 days.

(21) Appl. No.: 12/320,580

(22) Filed: Jan. 29, 2009

(65) Prior Publication Data
US 2009/0194695 A1 Aug. 6, 2009

(30) Foreign Application Priority Data
Jan. 31, 2008 (JP) ................. 2008-020768

(51) Int. Cl.
*G01T 1/00* (2006.01)
(52) U.S. Cl. ........... 250/336.1; 250/370.08; 250/370.09; 378/62
(58) Field of Classification Search ............ 250/336.1, 250/370.08, 370.09; 378/62
See application file for complete search history.

(56) References Cited

U.S. PATENT DOCUMENTS

| | | | | |
|---|---|---|---|---|
| 5,598,290 A | * | 1/1997 | Tanaka et al. | 398/195 |
| 2003/0004691 A1 | * | 1/2003 | Michiwaki et al. | 702/188 |
| 2003/0075670 A1 | * | 4/2003 | Tuominen | 250/205 |
| 2004/0240453 A1 | * | 12/2004 | Ikeda et al. | 370/395.21 |
| 2005/0075843 A1 | * | 4/2005 | Michiwaki et al. | 702/188 |
| 2006/0215807 A1 | * | 9/2006 | Ohara | 378/11 |
| 2006/0270385 A1 | * | 11/2006 | Morris | 455/405 |
| 2009/0124233 A1 | * | 5/2009 | Morris | 455/406 |

FOREIGN PATENT DOCUMENTS

| | | |
|---|---|---|
| JP | 3494683 | 6/1995 |
| JP | 2000-105297 | 4/2000 |
| JP | 2006-208306 | 8/2006 |

* cited by examiner

*Primary Examiner* — David Porta
*Assistant Examiner* — Djura Malevic
(74) *Attorney, Agent, or Firm* — Jean C. Edwards, Esq.; Edwards Neils PLLC

(57) ABSTRACT

A radiation conversion device is driven by an on-board battery, detects radiation that has passed through a subject, and converts the radiation into image information. A charging cradle to which the radiation conversion device is connected carries out a charging process on the battery. The radiation conversion device includes a signal transmitting unit for transmitting image information by wireless communications to an external apparatus, a transmission suspension unit for monitoring a transmission state of the image information by the signal transmitting unit and suspending transmission of the image information when a transmission error is generated, and a suspension release unit for releasing suspension of transmission of the image information when the radiation conversion device is connected to the charging cradle. The signal transmitting unit transmits the image information to the external apparatus when suspension of transmission of the image information has been released.

12 Claims, 5 Drawing Sheets

RADIATION CONVERSION DEVICE AND RADIATION IMAGE CAPTURING SYSTEM USING THE SAME

CROSS-REFERENCE TO RELATED APPLICATIONS

The present application claims priority from Japanese Patent Application No. 2008-020768, filed Jan. 31, 2008, the contents of which are herein incorporated by reference in their entirety.

BACKGROUND OF THE INVENTION

1. Field of the Invention

The present invention relates to a radiation conversion device, which is driven by an on-board battery mounted internally therein, for detecting radiation that has passed through a subject and converting the radiation into image information. The invention also concerns a radiation image capturing system that utilizes such a radiation conversion device.

2. Description of the Related Art

In the medical field, a radiation image capturing apparatus, in which radiation is applied to a subject, and radiation that has passed through the subject is directed to a radiation conversion device for capturing a radiation image of the subject, has been widely used.

In this case, a radiation conversion device (electronic cassette) is disclosed, in which applied radiation is converted directly into electric signals, or after the radiation has been converted into visible light by a scintillator, a plurality of radiation detection elements made up from amorphous silicon or the like, and which are arranged in a matrix form, are used to convert the visible light into electric signals to enable reading thereof. (See, Japanese Laid-Open Patent Publication No. 2006-208306.)

In the aforementioned radiation conversion device, a transportable type of structure with a battery is known, which can be carried from place to place. In such a transportable type of radiation conversion device, electrical power from an on-board battery is consumed when the radiation image is captured. Accordingly, the transportable radiation conversion device is connected to a charging cradle for carrying out charging of the battery at appropriate times. According to the radiation conversion device disclosed in Japanese Laid-Open Patent Publication No. 2006-208306, when the radiation conversion device is connected to the charging cradle, charging of the battery is carried out, together with transmitting radiation image information via the charging cradle to an external apparatus.

Notwithstanding, according to the disclosure of Japanese Laid-Open Patent Publication No. 2006-208306, after the radiation image has been captured, because a process for transmitting the radiation information is performed after the radiation conversion device has been connected to the charging cradle, a certain amount of time is spent before the transmission process commences, and the desired radiation image information cannot be acquired quickly. Consequently, it has been considered to transmit the radiation image information immediately after capturing the image, by means of wireless communications from the radiation conversion device directly to the external apparatus.

However, there are concerns that the residual charge amount of the on-board battery mounted in the radiation conversion device may become too low, or that transmission errors may occur upon transmission of the radiation image information by wireless communications to the external apparatus. In the case that data is transmitted via wireless communications, when transmission errors occur, normally the process for transmitting the data simply is repeated or carried out again. In this case, because power from the on-board battery mounted in the radiation conversion device is used, the frequency at which charging of the battery must be performed increases undesirably.

SUMMARY OF THE INVENTION

A general object of the present invention is to provide a radiation conversion device and a radiation image capturing system using the radiation conversion device, in which battery power is not consumed needlessly, and wherein image information can be effectively transmitted with respect to an external apparatus.

A principal object of the present invention is to provide a radiation conversion device and a radiation image capturing system using the radiation conversion device, in which battery power is not consumed needlessly, and wherein image information can be transmitted by means of wireless communications to an external apparatus.

The radiation conversion device of the present invention is characterized by a radiation conversion device driven by an on-board battery mounted therein, for detecting radiation that has passed through a subject and converting the radiation into image information, including a signal transmitting unit for transmitting the image information by wireless communications to an external apparatus, a transmission suspension unit for monitoring a transmission state of the image information by the signal transmitting unit and suspending transmission of the image information when a transmission error is generated, and a suspension release unit for releasing suspension of transmission of the image information when the radiation conversion device is connected to a charging cradle that charges the battery, wherein the signal transmitting unit transmits the image information to the external apparatus when suspension of transmission of the image information has been released.

In addition, a radiation image capturing system according to the present invention is characterized by a system including a radiation conversion device driven by an on-board battery mounted therein, for detecting radiation that has passed through a subject and converting the radiation into image information, and a charging cradle to which the radiation conversion device is connected for carrying out a charging process on the battery, in particular wherein the radiation conversion device further includes a signal transmitting unit for transmitting the image information by wireless communications to an external apparatus, a transmission suspension unit for monitoring a transmission state of the image information by the signal transmitting unit and suspending transmission of the image information when a transmission error is generated, and a suspension release unit for releasing suspension of transmission of the image information when the radiation conversion device is connected to a charging cradle that charges the battery, wherein the signal transmitting unit transmits the image information to the external apparatus when suspension of transmission of the image information has been released.

According to the present invention, when transmission of radiation image information is carried out from the radiation conversion device to an external apparatus, if transmission errors are generated, transmission of data is suspended. Then, when the radiation conversion device is connected to the charging cradle, the transmission of data is restarted. Accordingly, time can be utilized effectively, while the radiation image information can be transmitted efficiently.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
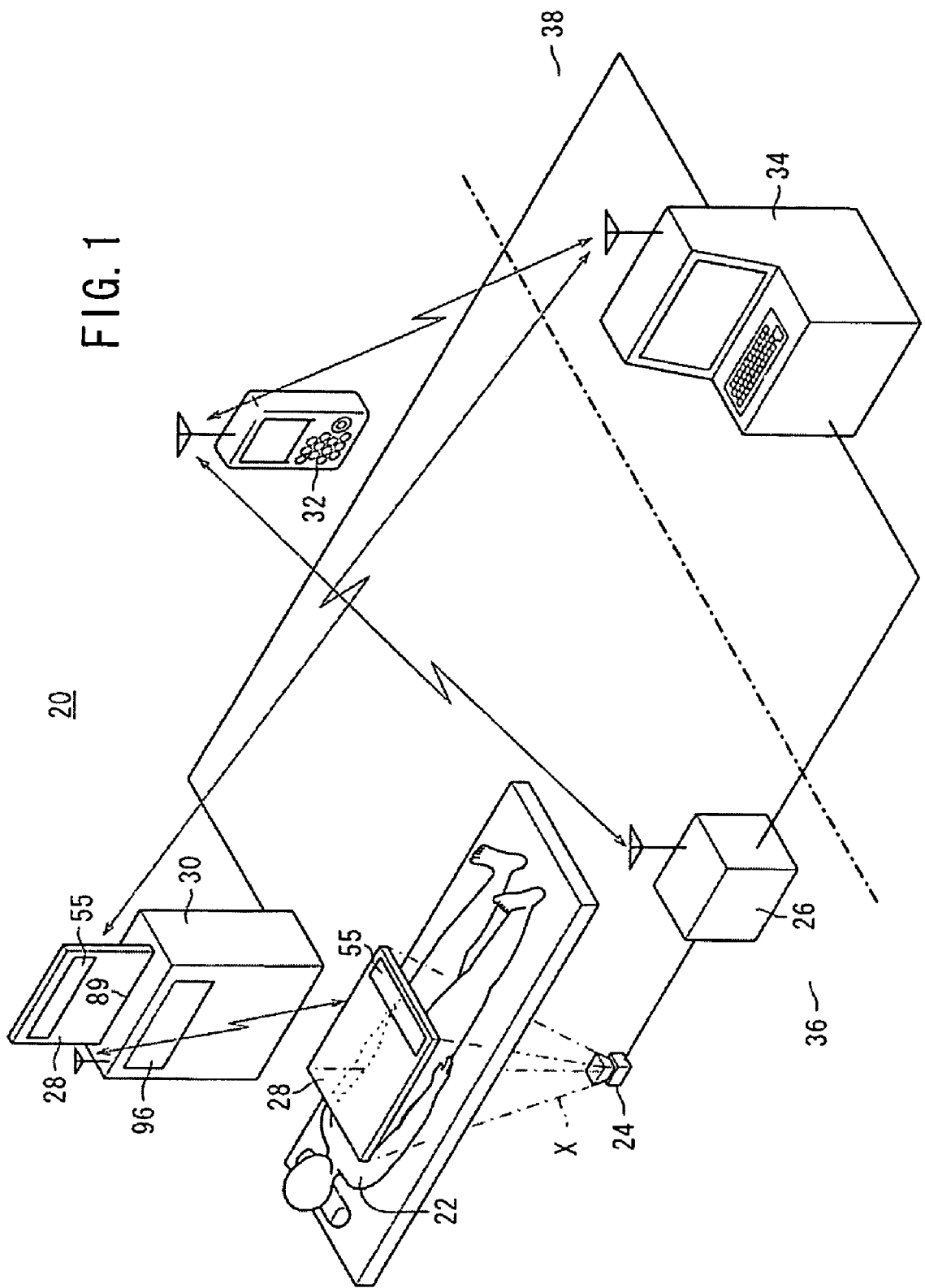
FIG. 1 is an explanatory view of a radiation image capturing system according to an embodiment of the present invention.

FIG. 1 is an explanatory view showing a radiation image capturing system 20 to which the radiation conversion device of the present invention is applied. The radiation image capturing system 20 is equipped with a radiation source 24 for irradiating a patient 22 (subject) with radiation X having a given dose according to image capturing conditions, a radiation source control device 26 for controlling the radiation source 24, an electronic cassette 28 (radiation conversion device) for converting the radiation X that has passed through the patient 22 into radiation image information, a cradle 30 for carrying out a charging process for the electronic cassette 28 as well as a transmitting and receiving process for the radiation image information, a portable information terminal 32 having an image capturing switch for the radiation source 24, and which is carried by a technician for confirming conditions including image capturing operations, and a console 34 (external apparatus), by which the radiation source control device 26, the cradle 30 and the portable information terminal 32 are controlled, while also setting necessary information, such as patient information, image capturing conditions and the like, and transmitting and receiving radiation image information therebetween.

The patient information is defined as information for specifying a patient 22, such as the name and sex of the patient 22, a patient ID number, and the like. The image capturing conditions are conditions for determining a tube voltage, a tube current, irradiation time, etc., for irradiating an imaging region of the patient 22 with an appropriate dose of radiation X. For example, the image capturing conditions may include the imaging region, the image capturing method, and the like. The patient information and the image capturing conditions can be obtained from the console 34.

The radiation source 24, the radiation source control device 26 and the cradle 30 are arranged inside of an image capturing room 36 where the image is to be captured, whereas the console 34 is disposed in an operations room 38 outside of the image capturing room 36. Further, necessary information is transmitted and received by wireless communications between the radiation source control device 26 and the portable information terminal 32, between the portable information terminal 32 and the console 34, between the electronic cassette 28 and the cradle 30, and between the cradle 30 and the console 34.

Figure 2:
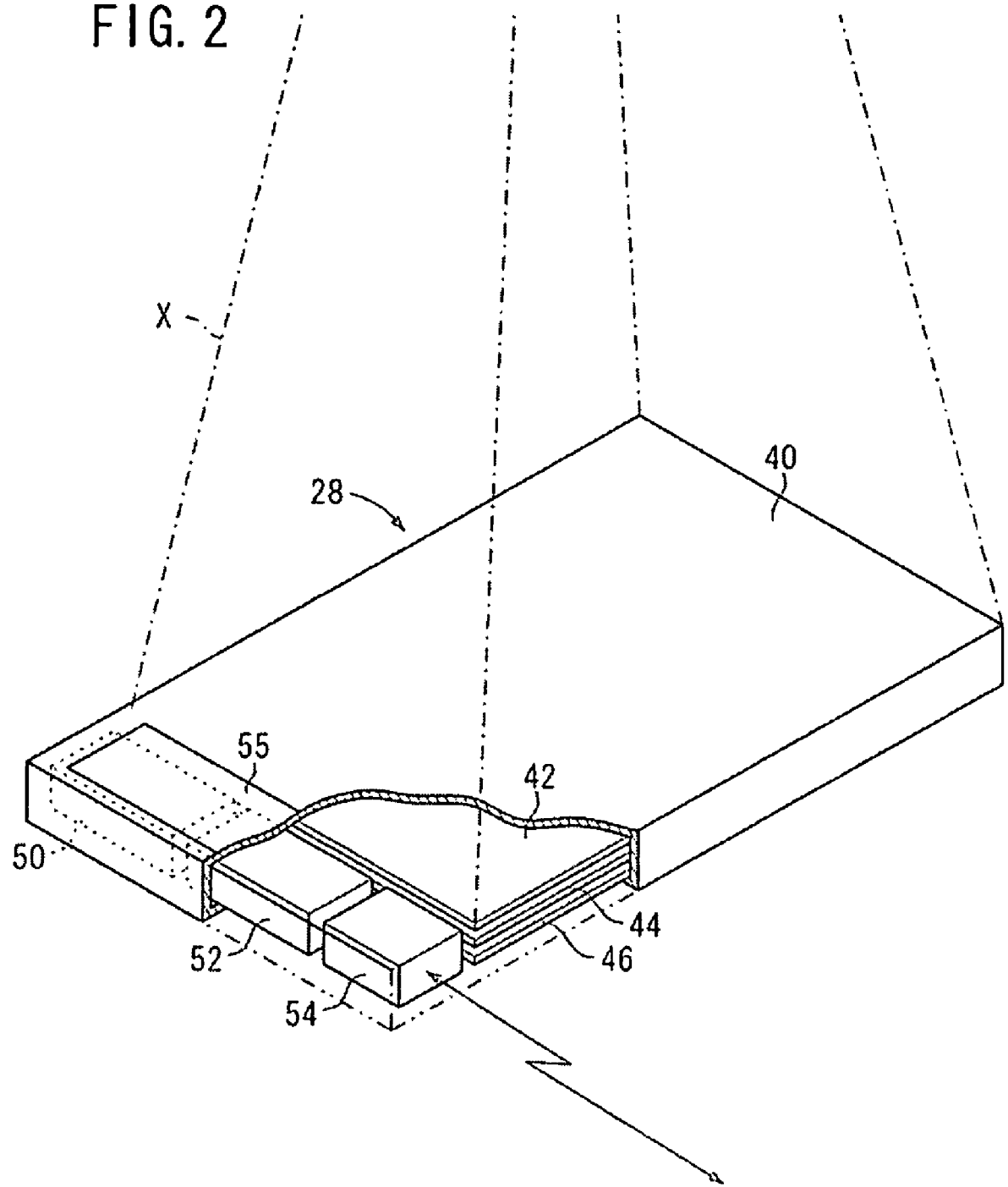
FIG. 2 is an internal structural view of an electronic cassette.

FIG. 2 is an internal structural view of the electronic cassette 28. The electronic cassette 28 is equipped with a casing 40 made from a material which is permeable to radiation X. Inside of the casing 40, a grid 42 for removing scattered radiation X from the patient 22, a radiation conversion panel 44 for detecting radiation X that has passed through the patient 22, and a lead plate 46 for absorbing backscattered radiation X are arranged in this order from the side on which radiation X is irradiated.

A battery 50 which serves as a power source for the electronic cassette 28, a controller 52 that controls driving of the radiation conversion panel 44 based on the power supplied from the battery 50, and a transceiver (signal transmitting/receiving unit) 54 for wirelessly transmitting signals to the cradle 30 including radiation image information converted into electrical signals from radiation X by the radiation conversion panel 44, are accommodated inside the casing 40. Moreover, in the controller 52 and the transceiver 54, for avoiding damage caused by radiation X, it is preferable for a lead plate or the like to be disposed on surface sides of the casing 40 that are subject to being irradiated with radiation X.

Further, on a surface of the casing 40 corresponding to a region where the battery 50, the controller 52 and the transceiver 54 are arranged, a display unit 55 is disposed, which displays image capturing conditions and patient information of the patient 22 whose image is to be captured by the electronic cassette 28, together with other information, including the residual charge amount of the battery 50 that drives the electronic cassette 28, and transmission information of the radiation image information.

Figure 3:
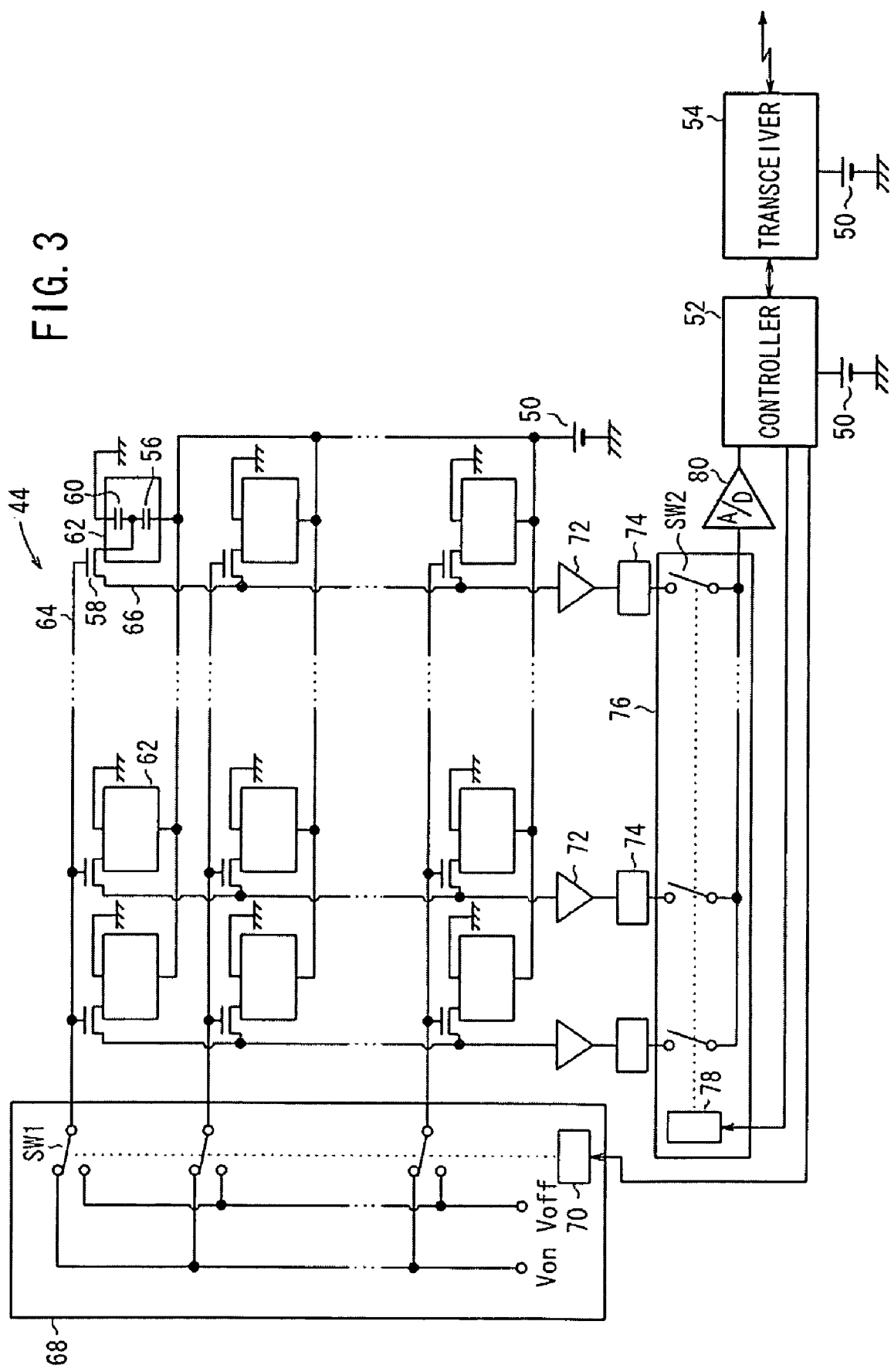
FIG. 3 is a schematic block diagram of the circuit configuration of a radiation conversion panel making up the electronic cassette.

FIG. 3 is a block diagram of a circuit configuration of the electronic cassette 28 including the radiation conversion panel 44 therein. The radiation conversion panel 44 includes a structure in which a photoelectric conversion layer 56 made up from an amorphous selenium (a-Se) material, which generates electric charges upon sensing radiation X, is disposed over thin film transistors (TFTs) 58 arrayed in a matrix form. After the generated electric charges are accumulated in storage capacitors 60, the TFTs 58 are successively turned on one line at a time, and the electric charges are read out as image signals. FIG. 3 shows the connected relationship of only one of the TFTs 58 and one pixel (image element) 62 made up from a photoelectric conversion layer 56 and a storage capacitor 60, whereas the structures of other similar pixels 62 have been omitted from illustration for the sake of simplicity. Since the structure of amorphous selenium changes and the functionality thereof is lowered at high temperatures, amorphous selenium must be used within a prescribed temperature range. Accordingly, it is preferable to provide some means for cooling the radiation conversion panel 44 inside the electronic cassette 28.

Gate lines 64, which extend in parallel to the direction of the rows, and signal lines 66 which extend in parallel to the direction of the columns, are connected to the TFTs 58, which are connected respectively to each of the pixels 62. Each of the gate lines 64 is connected to a line scanning driver 68, and each of the signal lines 66 is connected to a multiplexer 76 that constitutes a reading circuit.

Control signals Von, Voff that control ON and OFF states of the TFTs 58 arrayed in the direction of the rows, are supplied from the line scanning driver 68 to the gate lines 64. In this case, the line scanning driver 68 comprises a plurality of switches SW1 that switch the gate lines 64 on or off, and an address decoder 70, which outputs selection signals for selecting one of the switches SW1. Address signals are supplied from the controller 52 to the address decoder 70.

Further, the signal lines 66 are supplied with electric charges, which are stored in the storage capacitors 60 of each of the pixels 62, through the TFTs 58 arranged in the columns. The electric charges supplied to the signal lines 66 are amplified by amplifiers 72. The amplifiers 72 are connected through respective sample and hold circuits 74 to the multiplexer 76. The multiplexer 76 comprises a plurality of switches SW2 for successively switching between the signal lines 66, and an address decoder 78 for outputting a selection signal for selecting one of the switches SW2 at a time. The address decoder 78 is supplied with an address signal from the controller 52. An A/D converter 80 is connected to the multiplexer 76. A radiation image signal is converted by the A/D converter 80 into a digital image signal representing the radiation image information, which is supplied to the controller 52.

Figure 4:
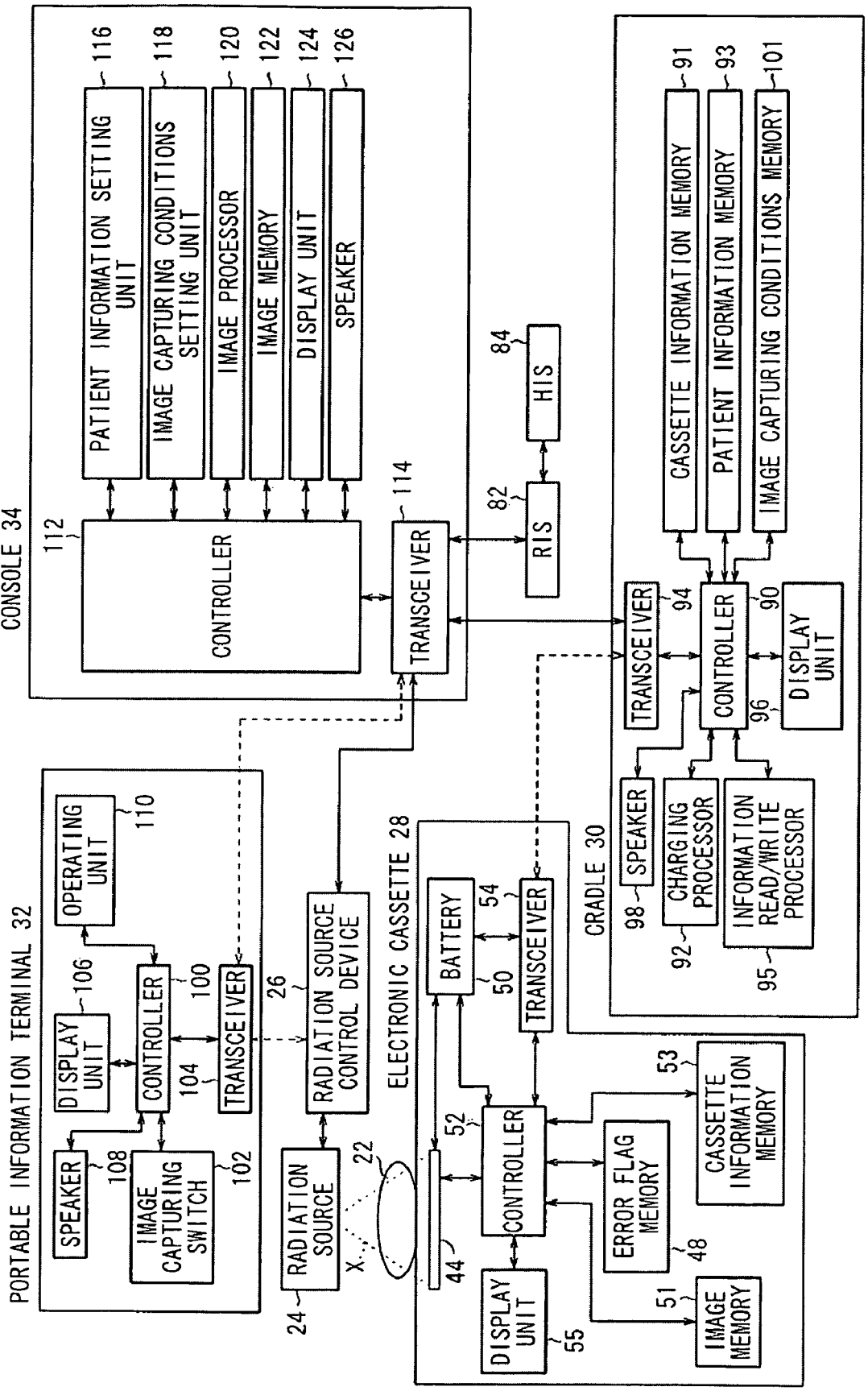
FIG. 4 is a schematic block diagram of the radiation image capturing system.

FIG. 4 is a schematic block diagram of the radiation image capturing system 20.

The radiation conversion panel 44, an image memory 51 for storing radiation image information detected by the radiation conversion panel 44, a cassette information memory 53 for storing cassette information comprising information specific to the electronic cassette 28, the display unit 55 for displaying cassette information, the transceiver 54, the battery 50 that supplies power to the electronic cassette 28, and an error flag memory 48 for recording an error flag which is set when a transmission error is generated, are connected respectively to the controller 52 of the electronic cassette 28.

The controller 52 monitors the signal transmission state of the radiation image information by the transceiver 54, and functions as an error flag setting unit for setting an error flag when a transmission error is generated. Further, the transceiver 54 functions as a transmission suspension unit for suspending transmission of the radiation image information when a transmission error is generated, as well as a suspension release unit for releasing suspension of transmission of the image information when the electronic cassette 28 is loaded into the cradle 30.

Herein, the cassette information can be defined to include, for example, information concerning the residual charge amount of the battery 50, patient information associated with radiation image information that is stored in the image memory 51, and an error flag, which is stored in the error flag memory 48. The patient information can be accessed and taken in from the cradle 30 or the console 34.

To a controller 90 of the cradle 30, there are connected respectively, a charging processor 92 that carries out a charging process on the battery 50 of the electronic cassette 28 loaded into a loading unit 89 (see FIG. 1), a cassette information memory 91 for storing cassette information obtained from the electronic cassette 28, a patient information memory 93 and an image capturing conditions memory 101 that store therein patient information and image capturing conditions obtained from the console 34, an information read/write processor 95 that writes in patient information and image capturing conditions to the electronic cassette 28 and also reads out cassette information and radiation image information from the electronic cassette 28, a display unit 96 for displaying necessary information including patient information, image capturing conditions and the acquired radiation image information, a speaker 98 for notifying a technician or the like concerning required information, and a transceiver (signal transmitting/receiving unit) 94 for carrying out transmission and reception of information between the electronic cassette 28 and the console 34. The transceiver 94 performs transmission and reception of signals with the electronic cassette 28 by means of wireless communications. Further, the charging process carried out with respect to the battery 50 of the electronic cassette 28 can be performed in a non-contact state through the transceiver 94, or in a contact state through a non-illustrated connector provided on the electronic cassette 28 loaded into the cradle 30.

A controller 100 of the portable information terminal 32 supplies an image capturing signal, which is generated by an image capturing switch 102 that drives the radiation source 24, to the radiation source control device 26 through a transceiver (signal transmitting/receiving unit) 104. Further, the controller 100 displays on a display unit 106 patient information, imaging capturing conditions, and the like, which are received from the console 34 through the transceiver 104, and also carries out processing for notifying a technician or the like by causing necessary information to be emitted from a speaker 108. The portable information terminal 32 includes an operating unit 110 by which necessary information can be set therein.

The console 34 is equipped with a controller 112, a transceiver (signal transmitting/receiving unit) 114 for transmitting and receiving necessary information via wireless communications with respect to the radiation source control device 26, the cradle 30 and the portable information terminal 32, a patient information setting unit 116 for setting patient information, an image capturing conditions setting unit 118 for setting necessary image capturing conditions for an image to be captured by the radiation source control device 26, an image processor 120 for performing image processing on the radiation image information, which is transmitted wirelessly from the electronic cassette 28 or supplied over wires from the electronic cassette 28 via the cradle 30, an image memory 122 for storing the processed radiation image information, a display unit 124 for displaying radiation image information and other necessary information, and a speaker 126 for notifying a technician or the like concerning the necessary information.

The console 34 is connected to a radiology information system (RIS) 82, which generally manages radiation image information handled by the radiological department of a hospital along with other information. The RIS 82 is connected to a hospital information system (HIS) 84, which generally manages medical information in the hospital. Image capturing order information, including the patient information and the image capturing conditions, may be set directly by the console 34, or alternatively, can be supplied to the console 34 from an external device via the RIS 82.

The radiation image capturing system 20 according to the present embodiment is constructed basically as described above. Next, explanations shall be made concerning operations of the radiation image capturing system 20.

When a radiation image of the patient 22 is to be captured, by using the patient information setting unit 116 of the console 34, patient information concerning the patient 22 is set, together with setting required image capturing conditions by using the image capturing conditions setting unit 118. Such information may be obtained from the RIS 82 and the HIS 84 from an upstream location via the transceiver 114. The thus set patient information and image capturing conditions can be displayed for confirmation on the display unit 124.

Next, the set patient information and image capturing conditions are transmitted from the transceiver 114 to the cradle 30, which is arranged inside the image capturing room 36, and the information and the conditions are displayed on the display unit 96 of the cradle 30 by the controller 90. In this case, the technician confirms the name of the patient 22, etc., whose image is to be captured, according to the patient information displayed on the display unit 96. By means of this confirmation process, accidents such as capturing an image by mistake of the wrong patient can be prevented from occurring. Further, according to the displayed image capturing conditions, the technician can confirm the imaging region, the image capturing method, etc.

On the other hand, the electronic cassette 28 used for capturing images is loaded into the cradle 30, and a charging process on the battery 50 is carried out by the charging processor 92. The information read/write processor 95 transmits patient information concerning the patient 22 whose image is being captured, together with the image capturing conditions, to the electronic cassette 28 via the transceiver 94. The controller 52 of the electronic cassette 28 stores the transmitted patient information and image capturing conditions in the cassette information memory 53, and displays the information and the conditions on the display unit 55. The display unit 55, as will be mentioned later, also can display the residual charge amount of the battery 50 of the electronic cassette 28, as well as transmission information of the radiation image information.

Further, the patient information and the image capturing conditions are transmitted from the transceiver 114 of the console 34 to the portable information terminal 32, which is carried by the technician, by means of wireless communications, and the patient information and the conditions are displayed on the display unit 106. In this case, the technician can confirm the patient information and the image capturing conditions that are displayed on the display unit 106 of the portable information terminal 32, so that desired preparations for capturing the image can be carried out.

Furthermore, the image capturing conditions are transmitted to the radiation source control device 26. The radiation source control device 26 sets the tube voltage, the tube current, and the irradiation time, which make up transmitted image capturing conditions, in the radiation source 24, thus carrying out preparations for capturing an image.

The technician confirms the patient information and the charge state, etc., of the electronic cassette 28, which are displayed on the display unit 96 of the cradle 30 or on the display unit 55 of the electronic cassette 28, and withdraws from the loading unit 89 of the cradle 30 a usable electronic cassette 28 in which the corresponding patient information has been set. According to the set image capturing conditions, the electronic cassette 28 is set on a desired imaging region of the patient 22.

After the electronic cassette 28 has been set in an appropriate condition with respect to the patient 22, the technician operates the image capturing switch 102 of the portable information terminal 32, whereupon capturing of the radiation image is carried out. When the image capturing switch 102 is operated, the controller 100 of the portable information terminal 32 transmits an image capture initiation signal to the radiation source control device 26 via the transceiver 104. The radiation source control device 26 that has received the image capture initiation signal controls the radiation source 24 according to the image capturing conditions supplied beforehand from the console 34, thereby irradiating the patient 22 with radiation X.

Radiation X that has passed through the patient 22, after scattered rays have been removed by the grid 42 of the electronic cassette 28, irradiate the radiation conversion panel 44 and are converted into electric signals by the photoelectric conversion layer 56 of each of the pixels 62 making up the radiation conversion panel 44, which are retained as charges in the storage capacitors 60 (see FIG. 3). Next, the electric charge information that forms the radiation image information of the patient 22 stored in each of the storage capacitors 60 is read out in accordance with address signals, which are supplied from the controller 52 to the line scanning driver 68 and the multiplexer 76.

More specifically, the address decoder 70 of the line scanning driver 68 outputs a selection signal according to the address signal supplied from the controller 52, thereby selecting one of the switches SW1, and supplies a control signal Von to the gate of the TFT 58 that is connected to a corresponding gate line 64. On the other hand, the address decoder 78 of the multiplexer 76 outputs a selection signal according to the address signal supplied from the controller 52, and successively switches the switches SW2, whereby the radiation image information, which is formed as electric charge information stored in the storage capacitors 60 of each of the pixels (image elements) 62 that are connected to the gate line 64 selected by the line scanning driver 68, is read out in succession through the signal lines 66.

The radiation image information read from the storage capacitors 60 of each of the pixels 62 connected to the selected gate line 64 of the radiation conversion panel 44 is amplified by respective amplifiers 72, sampled by the sample and hold circuits 74, and is supplied to the A/D converter 80 through the multiplexer 76 and converted into digital signals. The radiation image information having been converted into digital signals is temporarily stored in the image memory 51 connected to the controller 52.

Similarly, the address decoder 70 of the line scanning driver 68 successively turns on the switches SW1 according to the address signals supplied from the controller 52, and reads out the radiation image information, which is made up of charge information stored in the storage capacitors 60 of each of the pixels 62 connected respectively to the gate lines 64 through the signal lines 66, whereupon the radiation image information is temporarily stored in the image memory 51 connected to the controller 52 through the multiplexer 76 and the A/D converter 80.

Figure 5:
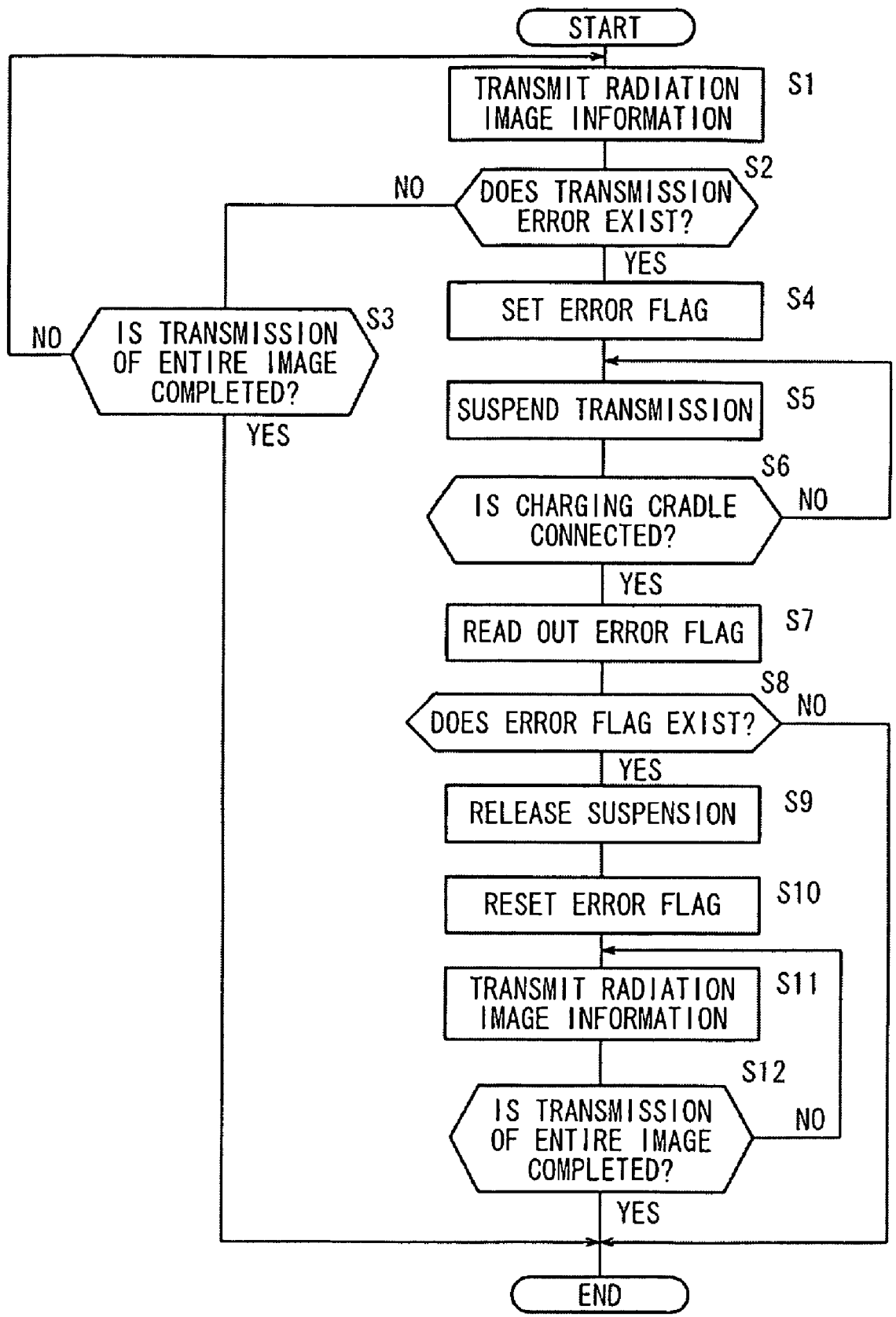
FIG. 5 is a flowchart of a transmission process of radiation image information from the electronic cassette to a cradle.

Upon completion of image capturing, the electronic cassette 28 in which radiation image information of the patient 22 has been recorded immediately begins a transmission process to the cradle 30 of the radiation image information stored in the image memory 51. Processing that is carried out in this case shall be explained in accordance with the flowchart shown in FIG. 5.

First, the controller 52 reads out the radiation image information from the image memory 51 and transmits the radiation image information to the cradle 30 through the transceiver 54 (step S1). The controller 52 monitors the transmission state of the radiation image information from the transceiver 54. In the case that a transmission error is not generated (step S2), transmission of the radiation image information continues until all of the radiation image information has been transmitted (step S3). The cradle 30, which has received the radiation image information via the transceiver 94, transmits the radiation image information to the console 34. After a predetermined image process by the image processor 120 has been performed with respect to the received radiation image information, the console 34 displays the radiation image information on the display unit 124. In this case, after capturing of the radiation image information, since the radiation image information is transmitted immediately to the console 34 via the cradle 30, the technician can very quickly confirm the acquired radiation image information.

On the other hand, in the event that a transmission error is generated during transmission of the radiation image information (step S2), the controller causes an error flag to be set in the error flag memory 48 (step S4), and transmission of the radiation image information to the cradle 30 is suspended immediately (step S5). In this case, by suspending transmission processing, needless consumption of power from the battery 50 is suppressed.

Consequently, when the controller 52 detects that the electronic cassette 28 has been loaded into the loading unit 89 of the cradle 30 and that the electronic cassette 28 and the cradle 30 are connected together (step S6), in the case that the controller 52 reads out the error flag from the error flag memory 48 (step S7) and the error flag is set (step S8), suspension of transmission processing of the radiation image information with respect to the cradle 30 is released (step S9), and the error flag stored in the error flag memory 48 is reset (step S10). The charging processor 92 of the cradle 30 then initiates a charging process with respect to the battery 50 mounted in the electronic cassette 28.

Next, the controller 52 of the electronic cassette 28 restarts transmission processing of the radiation image information with respect to the cradle 30 (step S11). In this case, since the electronic cassette is loaded into the cradle 30, and the transceiver 54 of the electronic cassette 28 is in close proximity to the transceiver 94 of the cradle 30, thereby assuring a favorable communications environment, transmission processing of the radiation image information can be carried out in a state where transmission errors are not generated. In this state, all of the radiation image information is transmitted to the cradle 30 (step S12).

In the foregoing manner, the entirety of the radiation image information, which has been transmitted to the cradle 30 from the electronic cassette 28, is in turn transmitted to the console 34 from the transceiver 94. By displaying the radiation image information on the display unit 124, confirmation of the image capturing conditions or the like can be performed. Transmission of the radiation image information from the cradle 30 to the console 34 is performed very quickly and reliably by wire communications.

Further, after compression processing has been effected, as may be required, on the radiation image information transmitted to the console 34, the radiation image information may be transmitted from the transceiver 114 to the portable information terminal 32, which is carried by the technician, and the information can be displayed as a preview image on the display unit 106. Further, a configuration may also be provided, in which the radiation image information is transmitted to the portable information terminal 32 directly from the cradle 30 or from the electronic cassette 28.

Of course, the present invention is not limited to the above-described embodiment, and the invention can be freely modified, within a range that does not deviate from the essence and gist of the present invention.

For example, the radiation conversion panel 44 accommodated in the electronic cassette 28 converts the dose of the radiation X directly into electric signals through the photoelectric conversion layer 56. However, in place of this structure, a radiation conversion panel in which radiation X is converted initially into visible light by a scintillator, and thereafter, the visible light is converted into electric signals using a solid-state detector element formed from amorphous silicon (a-Si) or the like, may also be used (see, Japanese Patent No. 3494683).

Further, the radiation image information can be obtained using a light-conversion type of radiation conversion panel. With such a light-conversion type of radiation conversion panel, radiation is irradiated onto respective solid state detection elements arranged in a matrix form, and an electrostatic latent image corresponding to the irradiation dose is stored cumulatively in the solid state detection elements. When the electrostatic latent image is read, reading light is irradiated onto the radiation conversion panel, and the generated current values are acquired as radiation image information. Further, by irradiating the radiation conversion panel with erasing light, the radiation image information in the form of a residual electrostatic latent image can be erased and the radiation conversion panel can be reused (see, Japanese Laid-Open Patent Publication No. 2000-105297).

What is claimed is:

1. A radiation conversion device driven by an on-board battery mounted therein, for detecting radiation that has passed through a subject and converting the radiation into image information, comprising:
   a signal transmitting unit for transmitting the image information by wireless communications to an external apparatus;
   a transmission suspension unit for monitoring a transmission state of the image information by the signal transmitting unit and suspending transmission of the image information when a transmission error is generated; and
   a suspension release unit for releasing suspension of transmission of the image information when the radiation conversion device is connected to a charging cradle that charges the battery,
   wherein the signal transmitting unit transmits the image information to the external apparatus when suspension of transmission of the image information has been released.

2. The radiation conversion device according to claim 1, wherein the signal transmitting unit transmits the image information to the external apparatus through the charging cradle.

3. The radiation conversion device according to claim 2, wherein the signal transmitting unit transmits the image information to the charging cradle by wireless communications, and
   the charging cradle transmits the image information by wire communications to the external apparatus.

4. The radiation conversion device according to claim 1, further comprising a display unit for displaying a transmission state of the image information.

5. The radiation conversion device according to claim 4, wherein the display unit displays a residual charge amount of the battery.

6. The radiation conversion device according to claim 1, wherein when the suspension of transmission of the image information is released by connecting the radiation conversion device to the charging cradle, the signal transmitting unit transmits the image information to the external apparatus by wireless communications.

7. A radiation image capturing system comprising:
   a radiation conversion device driven by an onboard battery mounted therein, for detecting radiation that has passed through a subject and converting the radiation into image information; and
   a charging cradle to which the radiation conversion device is connected for carrying out a charging process on the battery,
   the radiation conversion device further comprising:
   a signal transmitting unit for transmitting the image information by wireless communications to an external apparatus;
   a transmission suspension unit for monitoring a transmission state of the image information by the signal transmitting unit and suspending transmission of the image information when a transmission error is generated; and a suspension release unit for releasing suspension of transmission of the image information when the radiation conversion device is connected to a charging cradle that charges the battery, wherein the signal transmitting unit transmits the image information to the external apparatus when suspension of transmission of the image information has been released.

8. The radiation image capturing system according to claim 7, wherein the signal transmitting unit transmits the image information to the external apparatus through the charging cradle.

9. The radiation image capturing system according to claim 7, wherein the radiation conversion device comprises a display unit for displaying a transmission state of the image information.

10. The radiation image capturing system according to claim 9, wherein the display unit displays a residual charge amount of the battery.

11. The radiation image capturing system according to claim 7, wherein the signal transmitting unit transmits the image information to the charging cradle by wireless communications, and the charging cradle transmits the image information by wire communications to the external apparatus.

12. The radiation image capturing system according to claim 7, wherein when the suspension of transmission of the image information is released by connecting the radiation conversion device to the charging cradle, the signal transmitting unit transmits the image information to the external apparatus by wireless communications.

* * * * *